United States Patent [19]

Ashton et al.

[11] Patent Number: 4,960,775
[45] Date of Patent: Oct. 2, 1990

[54] PYRROLOPHTHALAZINES

[75] Inventors: Michael J. Ashton; Andrew W. Bridge, both of Chelmsford; Donald I. Dron, Upminster; Garry Fenton, Brentwood; David J. Lythgoe, Gidea Park; Christopher G. Newton, Chelmsford; David Riddell, Billericay; Christopher Smith, Benfleet; Keith A. J. Stuttle, Rockford, all of England

[73] Assignee: May & Baker Limited, Dagenham, England

[21] Appl. No.: 279,123

[22] Filed: Dec. 2, 1988

[30] Foreign Application Priority Data

Dec. 3, 1987 [GB] United Kingdom ............ 872314

[51] Int. Cl.$^5$ ............... A61K 31/50; C07D 487/04
[52] U.S. Cl. .................. 514/248; 544/229; 544/234; 544/237
[58] Field of Search ............... 544/234; 514/248

[56] References Cited

U.S. PATENT DOCUMENTS 4,369,318  1/1983  Jan ............................ 544/234
4,855,297  8/1989  Fischer et al. ............. 544/234
4,889,854 12/1989  Widmer ..................... 514/248

Primary Examiner—Nicholas S. Rizzo
Assistant Examiner—E. Benhardt
Attorney, Agent, or Firm—Stevens, Davis, Miller & Mosher

[57] ABSTRACT

Therapeutically useful pyrrolo[2,1-a]phthalazine derivatives of the formula:

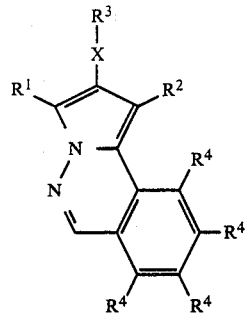

wherein $R^1$ and $R^2$ represent cycloalkyl, optionally substituted alkyl, alkenyl, alkynyl, aryl or heteroaryl, X represents ethylene or vinylene, $R^3$ represents a group of the formula:

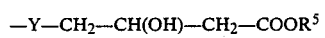

$$-Y-CH_2-CH(OH)-CH_2-COOR^5$$

wherein Y represents carbonyl or hydroxymethylene and $R^5$ represents hydrogen or optionally substituted alkyl, or $R^3$ represents a lactone ring and the symbols $R^4$ represent hydrogen, halogen, optionally substituted alkyl, alkenyl, alkynyl, aryl or heteroaryl, or $R^6O-$ wherein $R^6$ represents alkyl, aryl or arylalkyl and salts thereof, processes for their preparation and compositions containing them are described.

16 Claims, No Drawings

PYRROLOPHTHALAZINES

The present invention relates to new therapeutically useful pyrrolo[2,1-a]phthalazine derivatives, to processes for their preparation, to pharmaceutical compositions containing them, and to their use as pharmaceuticals.

The pyrrolo[2,1-a]phthalazine derivatives are the compounds of general formula I shown hereinafter in the present specification, wherein $R^1$ and $R^2$, which may be the same or, preferably, different, each represents a cycloalkyl group containing from 3 to 8 carbon atoms, or represents a straight- or branched-chain alkyl, alkenyl or alkynyl group containing up to 6 carbon atoms, which may be substituted by up to three halogen, preferably chlorine or fluorine, atoms, or represents an optionally substituted aryl, preferably phenyl, or heteroaryl group, X represents an ethylene or vinylene group, preferably a vinylene group in the E-configuration, $R^3$ represents a group of the general formula:

$$-Y-CH_2-CH(OH)-CH_2-COOR^5 \qquad II$$

wherein Y represents a carbonyl or hydroxymethylene group and $R^5$ represents a hydrogen atom or an optionally substituted alkyl group containing up to 6 carbon atoms, or $R^3$ represents a lactone ring of general formula III shown hereinafter in the specification, and the symbols $R^4$ may be the same or different and each represents a hydrogen or halogen (i.e. fluorine, chlorine, bromine or iodine) atom, or represents an optionally substituted straight- or branched-chain alkyl, alkenyl or alkynyl group containing up to 6 carbon atoms, or an optionally substituted aryl, preferably phenyl, or heteroaryl group, or a group of the formula $R^6O-$ wherein $R^6$ represents a straight- or branched-chain alkyl group containing up to 6 carbon atoms, an aryl, e.g. phenyl, group or an arylalkyl group containing 1 or 2 carbon atoms in the alkyl moiety, e.g. benzyl or phenethyl, and pharmaceutically acceptable salts thereof when $R^5$ represents a hydrogen atom, for example alkali metal, alkaline earth metal, ammonium and amine salts.

It is to be understood that, where in this specification reference is made to compounds of formula I, it is intended to refer also where the context so permits to their pharmaceutically acceptable salts.

Substituted alkyl, alkenyl or alkynyl groups within the definition of formula I unless otherwise specified preferably carry up to three substituents selected from halogen, preferably fluorine or chlorine, atoms and straight- or branched-chain alkoxy and alkylthio groups each containing up to 6 carbon atoms.

Substituted aryl and heteroaryl groups and moieties within the definition of formula I preferably carry one or more substituents selected from halogen, preferably fluorine or chlorine, atoms, cycloalkyl and cycloalkenyl groups each containing from 4 to 8 carbon atoms, and optionally substituted straight- or branched-chain alkyl, alkenyl or alkynyl groups each containing up to 6 carbon atoms.

As will be appreciated by those skilled in the art, the compounds of formula I may exist in various isomeric forms, for example diastereoisomeric forms, and all such forms and mixtures thereof are included within the scope of the invention. However, when $R^3$ represents a group of formula II and Y represents a hydroxymethylene group the erythro-form is the preferred form. When $R^3$ represents a group of formula III the preferred form has the hydroxy group attached to the lactone ring in the trans-configuration with respect to the rest of the molecule.

Preferably the lactone ring of formula III is the isomer which has the (4R,6S)-configuration when X represents vinylene and the (4R,6R)-configuration when X represents ethylene.

The compounds of formula I possess useful pharmacological properties, and some are useful as intermediates for the preparation of other therapeutically useful compounds, for example other compounds of formula I, for example as described later in this specification.

For example they lower the concentrations of cholesterol and of low density lipoproteins in the blood. Thus they are of utility in the prevention or treatment of hypercholesterolaemic and hyperlipoproteinaemic states, of atherosclerosis, and of associated conditions such as angina, myocardial infarction, cerebral vascular occlusion, arterial aneurism, peripheral vascular disease, recurrent pancreatitis, xanthomas and fungal infections, e.g. candidiasis.

Particularly important classes of compounds of formula I include those which exhibit one or more of the following features:

(i) one of $R^1$ and $R^2$, preferably $R^2$, represents an optionally substituted aryl or heteroaryl group, more particularly a substituted or unsubstituted phenyl group, for example a phenyl group substituted by a halogen, e.g. fluorine, atom, especially in the 4-position of the phenyl group, and the other one of $R^1$ and $R^2$, preferably $R^1$, represents a cycloalkyl group containing from 3 to 8 carbon atoms, or a straight- or branched-chain alkyl, alkenyl or alkynyl group containing up to 6 carbon atoms, which may be substituted by up to 3 halogen, preferably chlorine or fluorine, atoms, more particularly a straight- or branched-chain alkyl group, for example an isopropyl group;

(ii) X represents a trans-vinylene group;

(iii) $R^5$ represents a hydrogen atom or a methyl or ethyl group; and/or (iv) the symbols $R^4$ all represent hydrogen atoms; the other symbols being as hereinbefore defined and, more especially, their pharmaceutically acceptable salts, particularly the alkali metal, e.g.sodium, salts.

Important compounds of formula I include the following:

| | |
|---|---|
| 3:2 mixture of erythro- and threo-diastereoisomers of ethyl (E)-3,5-dihydroxy-7-(3-isopropyl-1-phenylpyrrolo[2,1-a]phthalazin-2-yl)hept-6-enoate; | A |
| 3:2 mixture of erythro- and threo-diastereoisomers of sodium (E)-3,5-dihydroxy-7-(3-isopropyl-1-phenylpyrrolo[2,1-a]phthalazin-2-yl)hept-6-enoate; | B |
| 3:2 mixture of erythro- and threo-diastereoisomers of ethyl (E)-7-{1-(4-fluorophenyl)-3-isopropyl-pyrrolo[2,1-a]phthalazin-2-yl}-3,5-dihydroxyhept-6-enoate; | C |
| ethyl erythro-(E)-7-{(1-(4-fluorophenyl)-3-isopropylpyrrolo[2,1-a]phthalazin-2-yl}-3,5-dihydroxyhept-6-enoate; | CA |
| ethyl threo-(E)-7-{1-(4-fluorophenyl)-3-isopropyl-pyrrolo[2,1-a]phthalazin-2-yl}-3,5-dihyroxy-hept-6-enoate; | CB |
| 3:2 mixture of erythro- and threo-diastereoisomers of sodium (E)-7-{1-(4-fluorophenyl)-3-isopropyl-pyrrolo[2,1-a]phthalazin-2-yl}-3,5-dihydroxy-hept-6-enoate; | D |
| sodium erythro-(E)-7-{1-(4-fluorophenyl)-3-isopropylpyrrolo[2,1-a]phthalazin-2-yl}-3,5-dihydroxyhept-6-enoate; | DA |
| sodium threo-(E)-7-{1-(4-fluorophenyl)-3- | DB |

-continued isopropylpyrrolo[2,1-a]phthalazin-2-yl)-3,5-dihydroxyhept-6-enoate;
methyl (E)-7-{1-(4-fluorophenyl)-3-isopropyl-pyrrolo[2,1-a]phthalazin-2-yl}-3,5-dihydroxy-hept-6-enoate;  E
methyl (E)-7-{1-(4-fluorophenyl)-3-isopropyl-pyrrolo[2,1-a]phthalazin-2-yl}-3-hydroxy-5-oxohept-6-enoate; and  F
sodium (E)-7-{1-(4-fluorophenyl)-3-isopropyl-pyrrolo[2,1-a]phthalazin-2-yl}-3-hydroxy-5-oxohept-6-enoate.  G The letters A to G are allocated to the compounds for easy reference later in this specification.

Compounds B and, especially, D are of particular importance, especially their erythro-components, e.g. compound DA.

In tests, the compounds of formula I show good results as competitive inhibitors of 3-hydroxy-3-methyl-glutaryl coenzyme A (HMG CoA) reductase and as a consequence are inhibitors of cholesterol biosynthesis.

For example, in tests compounds of formula I produced inhibition in rat hepatic microsomal HMG CoA reductase activity in vitro as shown in the following Table I.

In the table the concentrations of the test compounds are expressed in micrograms/ml.

TABLE I

| Compound | Concentration | % Inhibition |
|---|---|---|
| B | 20.0 | 98 |
|   | 6.67 | 90 |
|   | 2.22 | 74 |
|   | 0.74 | 56 |
|   | 0.25 | 38 |
| CA | 6.66 | 95 |
|   | 2.22 | 85 |
|   | 0.74 | 65 |
|   | 0.24 | 47 |
|   | 0.082 | 33 |
|   | 0.027 | 23 |
| D | 6.67 | 90 |
|   | 2.22 | 76 |
|   | 0.74 | 66 |
|   | 0.25 | 61 |
|   | 0.082 | 50 |
|   | 0.027 | 47 |
| DA | 6.66 | 98 |
|   | 2.22 | 94 |
|   | 0.74 | 86 |
|   | 0.24 | 72 |
|   | 0.082 | 58 |
|   | 0.027 | 49 |
| DB | 6.66 | 85 |
|   | 2.22 | 67 |
|   | 0.74 | 52 |
|   | 0.24 | 45 |
|   | 0.082 | 34 |
|   | 0.27 | 29 |
| G | 20.0 | 92 |
|   | 6.66 | 77 |
|   | 2.22 | 52 |
|   | 0.74 | 29 |

Compounds of formula I and intermediates for their preparation may be prepared by the application or adaptation of known methods, for example methods similar to those described hereinafter in the following Examples and Reference Examples.

Optionally the reactions may be carried out in an inert atmosphere.

For example, according to a feature of the invention, compounds of formula I wherein $R^3$ represents a group of formula II, Y represents a hydroxymethylene group, $R^5$ represents an optionally substituted alkyl group containing up to 6 carbon atoms and $R^1$, $R^2$, $R^4$ and X are as hereinbefore defined, are prepared by the reduction of compounds of general formula IV shown hereinafter in the specification, wherein $R^1$, $R^2$, $R^4$ and X are as hereinbefore defined and $R^7$ represents a group of the general formula:

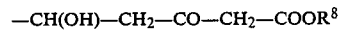

$$-CH(OH)-CH_2-CO-CH_2-COOR^8 \quad V$$

wherein $R^8$ represents an optionally substituted alkyl group containing up to 6 carbon atoms. The reduction may be carried out by means of sodium borohydride, preferably in a lower alkanol, e.g. methanol, and preferably below room temperature, e.g. at or near to 0° C. It should be noted that by prolonging the reaction time transesterification can also occur, if the alkyl group in the said lower alkanol does not correspond to the value of $R^5$ in the starting material of formula V.

According to a further feature of the invention, compounds of formula I wherein $R^3$ represents a group of formula II wherein $R^5$ represents a hydrogen atom ($R^1$, $R^2$, $R^4$ and X being as hereinbefore defined), or salts thereof, are prepared from the corresponding compounds wherein $R^5$ represents an optionally substituted alkyl group containing up to 6 carbon atoms by hydrolysis by known methods, for example by reaction with an aqueous solution of the corresponding base to form the salt, optionally followed by acidification to form the parent carboxylic acid.

According to a further feature of the invention, compounds of formula I wherein $R^3$ represents a group of formula II, wherein Y represents a carbonyl group, $R^1$, $R^2$, $R^4$, $R^5$ and X being as hereinbefore defined, are prepared by the oxidation of the corresponding compounds wherein Y represents a hydroxymethylene group. The oxidation may be carried out by reaction with activated manganese dioxide, preferably at or near room temperature.

According to a further feature of the invention, compounds of formula I wherein X represents an ethylene group, $R^1$, $R^2$, $R^3$ and $R^4$ being as hereinbefore defined, are prepared from corresponding compounds wherein X represents a vinylene group, by catalytic hydrogenation. Suitable catalysts include those containing palladium, e.g. palladium on charcoal or on calcium carbonate, or mixtures thereof.

According to a further feature of the invention, compounds of formula I wherein $R^3$ represents a lactone ring of formula III, $R^1$, $R^2$, $R^4$, and X being as hereinbefore defined, are prepared by the cyclisation of the corresponding compounds wherein $R^3$ represents a group of formula II, wherein Y represents a hydroxymethylene group and $R^5$ represents a hydrogen atom. Sometimes the cyclisation occurs spontaneously but sometimes it is preferable to warm or to heat the starting material. Conveniently the heating is carried out in a solvent such as toluene at temperatures up to the boiling point. Optionally the reaction is carried out in the presence of a trace of an acid, e.g. glacial acetic acid.

The pharmaceutically acceptable salts may be prepared from parent compounds of formula I by known methods, for example by reaction of compounds of formula I (wherein $R^3$ represents a group of formula II in which $R^5$ represents a hydrogen atom) and the appropriate base, e.g. an alkali metal hydroxide or carbonate, an alkaline earth metal oxide, ammonia or an amine, in a suitable solvent which is preferably water in the case of the preparation of alkali and alkaline earth metal salts and water or isopropanol in the case of amine salts.

As well as being useful in themselves as pharmaceutically useful compounds, salts of the compounds of formula I wherein $R^3$ represents a group of formula II wherein $R^5$ represents a hydrogen atom are useful for the purpose of purification of the parent acids of formula I, for example by exploitation of the solubility differences between the salts and the parent acids in water and in organic solvents, by techniques well known to those skilled in the art. The parent acids of formula I can be regenerated from their salts by known methods, for example by treatment with a mineral acid, e.g. dilute hydrochloric acid, or an organic acid, e.g. acetic acid.

As will be readily appreciated by those skilled in the art, the compounds of formula I, including their aforementioned isomers, may be separated by the application or adaptation of known methods. For example, diastereoisomeric forms may be separated by chromatography using selective adsorption from solution or from the vapour phase onto suitable adsorbents, and enantiomeric forms of compounds of formula I wherein $R^3$ represents a group of formula II in which $R^5$ represents a hydrogen atom may be separated by formation of salts with an optically active base, followed by separation of the obtained pair of diastereoisomers by, for example, fractional crystallisation from a suitable solvent system, followed by separate regeneration of the enantiomeric acids.

Compounds of formula IV may be prepared by the application or adaptation of known methods, for example methods illustrated in the following Reference Examples.

By the term "known methods" as used in this specification is meant methods used heretofore or known in the literature. For example, compounds of formula IV wherein X represents an ethylene group and $R^1$, $R^2$, $R^4$ and $R^7$ are as hereinbefore defined, may be prepared by the catalytic reduction of corresponding compounds wherein X represents a vinylene group, under conditions similar to those described hereinbefore for the preparation of compounds of formula I wherein X represents an ethylene group by catalytic reduction.

Compounds of formula IV, wherein $R^1$, $R^2$, $R^4$, $R^7$ and X are as hereinbefore defined, may be prepared from compounds of the general formula VI shown hereinafter in the specification, wherein $R^1$, $R^2$, $R^4$ and X are as hereinbefore defined, by reaction with a dianion of a compound of the general formula:

$$CH_3COCH_2COOR^8 \qquad \qquad VII$$

wherein $R^8$ is as hereinbefore defined, generated in situ by treatment with two equivalents of strong base, for example sodium hydride and/or butyl lithium, in a suitable solvent such as tetrahydrofuran and at between $-50°$ C. and $0°$ C.

Compounds of formula VI, wherein $R^1$, $R^2$, $R^4$ and X are as hereinbefore defined, may be prepared by the oxidation of compounds of the general formula VIII shown hereinafter in the specification, wherein $R^1$, $R^2$, $R^4$ and X are as hereinbefore defined, under conditions similar to those described hereinbefore for the preparation of compounds of formula I wherein Y represents a carbonyl group by oxidation.

Compounds of formula VIII, wherein $R^1$, $R^2$, $R^4$ and X are as hereinbefore defined, may be prepared by the reduction of compounds of the general formula IX shown hereinafter in the specification, wherein $R^1$, $R^2$, $R^4$ and X are as hereinbefore defined and $R^9$ represents an alkyl group of 1 to 4 carbon atoms, for example by means of di-isobutylaluminium hydride in a suitable solvent such as tetrahydrofuran and between $-30°$ C. and $+30°$ C.

Compounds of formula IX wherein X represents a vinylene group, and $R^1$, $R^2$, $R^4$ and $R^9$ are as hereinbefore defined, may be prepared from a compound of the general formula X shown hereinafter in the specification, wherein $R^1$, $R^2$ and $R^4$ are as hereinbefore defined, by a Wittig reaction, or variant thereof, for example by reaction with the anion of a trialkyl phosphonoacetate (generated in situ by treatment with a strong base, for example sodium hydride), in a suitable solvent such as tetrahydrofuran and at between $-20°$ C. and $50°$ C.

Compounds of formula IX wherein X represents an ethylene group, and $R^1$, $R^2$, $R^4$ and $R^9$ are as hereinbefore defined, may be prepared by the catalytic reduction of corresponding compounds wherein X represents vinylene group, under conditions similar to those described hereinbefore for the preparation of compounds of formula I wherein X represents an ethylene group by catalytic reduction.

Compounds of formula X, wherein $R^1$, $R^2$ and $R^4$ are as hereinbefore defined, may be prepared from a compound of the general formula XI shown hereinafter in the specification, wherein $R^1$, $R^2$ and $R^4$ are as hereinbefore defined and $R^{10}$ represents an alkyl group of 1 to 4 carbon atoms, by a series of reactions similar to those described hereinbefore for the preparation of compounds of formula VI from compounds of formula IX.

Compounds of formula XI, wherein $R^1$, $R^2$, $R^4$ and $R^{10}$ are as hereinbefore defined, may be prepared from a compound of the general formula XII shown hereinafter in the specification, wherein $R^1$ and $R^4$ are as hereinbefore defined, by reaction with a compound of the general formula:

$$R^2C\equiv CCOOR^{10} \qquad \qquad XIII$$

wherein $R^2$ and $R^{10}$ are as hereinbefore defined in a suitable solvent, for example acetonitrile or 1,3-dimethylimidazolin-2-one, at $10°-100°$ C.

Compounds of formula XII, wherein $R^1$ and $R^4$ are as hereinbefore defined, may be prepared from a compound of the general formula XIV shown hereinafter in the specification, wherein $R^1$ and $R^4$ are as hereinbefore defined, by reaction with a mixture of acetic acid and fluoroboric acid at $10°-80°$ C.

Compounds of formula XIV, wherein $R^1$ and $R^4$ are as hereinbefore defined, may be prepared from a compound of the general formula XV shown hereinafter in the specification, wherein $R^4$ is as hereinbefore defined, by reaction with a compound of the general formula:

$$R^1COZ \qquad \qquad XVI$$

wherein $R^1$ is as hereinbefore defined and Z represents a halogen atom, preferably a chlorine atom, in the presence of an alkali metal cyanide in a suitable solvent, for example dichloromethane, at $0°-50°$ C. or, preferably, in the presence of a trialkylsilylcyanide, for example trimethylsilylcyanide, preferably in the presence of a catalytic amount of a Lewis acid, for example aluminium chloride, in a suitable solvent, for example dichloromethane, at $0°-50°$ C.

Intermediate compounds of general formulae VII, XIII, XV and XVI, wherein the various symbols are as hereinbefore defined, are known or can be prepared by the application or adaptation of known methods.

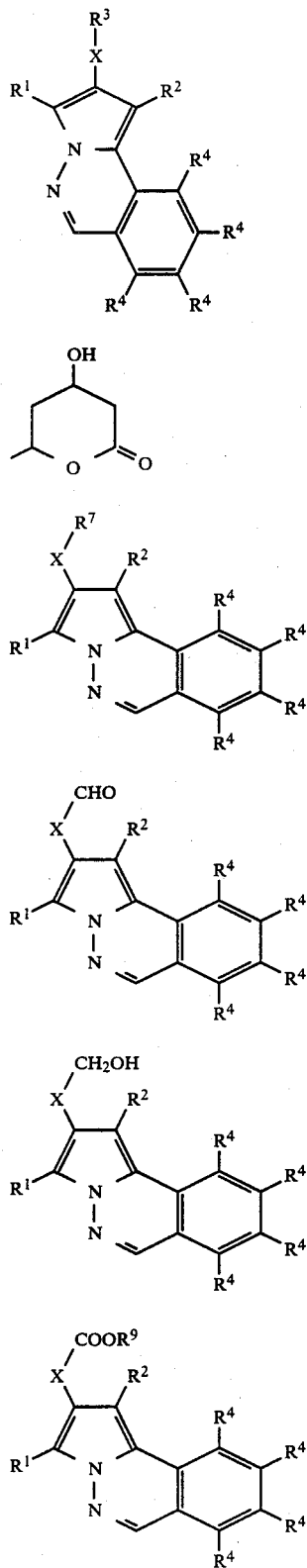

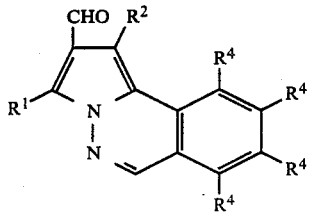

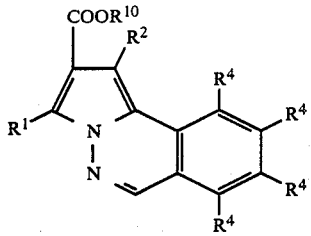

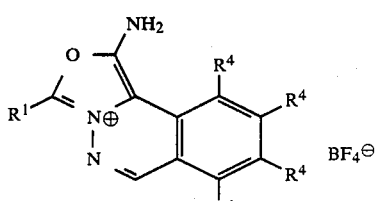

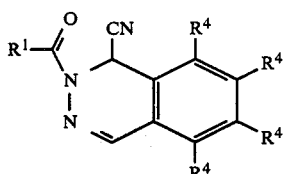

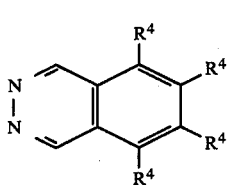

The following Examples illustrate the preparation of compounds according to the present invention, and the Reference Examples illustrate the preparation of intermediates.

In the presentation of the nuclear magnetic resonance ("NMR") spectra, "DMSO-$d_6$" means "deuterated dimethylsulphoxide", "s", "d", "t", "q" and "m" mean "singlet", "doublet", "triplet", "quartet" and "multiplet" respectively, "dd" means "doublet of doublets" and "dt" means "doublet of triplets", and the positions of the signals are given in parts per million from the tetramethylsilane signal.

EXAMPLE 1

Compound A

A stirred solution of ethyl (E)-5-hydroxy-7-(3-isopropyl-1-phenylpyrrolo[2,1-a]phthalazin-2-yl) -3-oxohept-6-enoate [0.32 g; prepared as described in Reference Example 1(i)]in methanol (10 ml) under an atmosphere of argon was cooled to 0° C and treated with sodium borohydride (15.2 mg). The solution was stirred for 15 minutes and then it was poured into a mixture of ice and water (50 ml). The resulting mixture was extracted with diethyl ether (100 ml) and then with ethyl acetate (2×50 ml). The combined extracts were dried over magnesium sulphate, evaporated and subjected to flash chromatography on silica gel, using as eluant a mixture of petroleum ether (b.p. 40-60° C) and diethyl ether (1:1 v/v), to give ethyl (E)-3,5-dihydroxy-7-(3-isopropyl-1-phenylpyrrolo[2.1-a]phthalazin-2-yl)-hept -6-enoate (0.26 g) in the form of a yellow gum. [NMR (in a mixture of $CDCl_3$ and $D_2O$): 1.28 (3 H, t, J=7 Hz), 1.4–1.7 (2 H, m), 1.52 (6 H, d, J=7 Hz), 2.40–2.48 (2 H, m), 3.8 (1H, septet, J=7 Hz), 4.08–4.14 (3 H, m), 4.28–4.42 (1 H, m), 5.31 and 5.36 (1 H, two dd, J=16 Hz, 6 Hz), 6.63 and 6.65 (1 H, two dd, J=16 Hz, 1 Hz), 7.22–7.64 (9 H, m), 8.24 (1 H, s)].

The NMR spectrum indicated that the product was a 3:2 mixture of the erythro- and threo-diastereoisomers.

EXAMPLE 2

Compound B

A solution of a 3:2 mixture of the erythro- and threo-isomers of ethyl (E)-3,5-dihydroxy-7-(3-isopropyl-1-phenylpyrrolo[2,1-a]phthalazin-2-yl)-hept -6-enoate (0.26 g; prepared as described in Example 1) and sodium hydroxide (22 mg) in water (1.0 ml) and methanol (10 ml) was stirred at the ambient temperature under an atmosphere of argon for 3 hours. The solution was then evaporated in vacuo and the residue was dried by treatment twice with methanol (2×10 ml) and once with diethyl ether (10 ml) followed each time by evaporation in vacuo, finally drying under high vacuum, to give sodium (E)-3,5-dihydroxy-7-(3-isopropyl-1-phenylpyrrolo[2,1-a]phthalazin-2-yl)-hept-6-enoate (0.21 g) in the form of a yellow solid, m.p. 209°–215° C. [Elemental analysis: C, 65.8; H, 6.1; N, 5.4; $H_2O$, 4.9%; calculated for $C_{27}H_{27}$ $N_2O_4Na:1.5H_2O$: C, 65.7; H, 6.13; N, 5.7; $H_2O$, 5.5%; NMR (in a mixture of DMSO-d6 and $D_2O$): 1.10–1.32 (2 H, m), 1.5 (6 H, d, J=7 Hz), 1.7–2.1 (2 H, m), 3.50–3.86 (2 H, m), 4.02–4.16 (1 H, m), 5.28 and 5.36 (1 H, two dd, J=16 Hz, 6 Hz), 6.46 (1 H, dd, J=16 Hz, 1 Hz), 7.16–7.60 (8 H, m), 7.78–7.88 (1 H, m), 8.57 (1 H, s)].

The NMR spectrum indicated that the product was a 3:2 mixture of the erythro- and threo-diastereoisomers.

EXAMPLE 3

Compound C

By proceeding in a manner similar to that described hereinbefore in Example 1, but using as the starting material the appropriate quantity of ethyl (E)-7-{1-(4-fluorophenyl)-3-isopropylpyrrolo[2,1-a]phthalazin-2-yl}-5-hydroxy-3-oxohept-6-enoate [prepared as described in Reference 2(g)], there was prepared ethyl (E)-7-{1-(4-fluorophenyl)-3-isopropylpyrrolo-[2,1-a]phthalazin-2-yl}-3,5-dihydroxyhept-6-enoate, in the form of a yellow gum.

EXAMPLE 4

Compound D

By proceeding in a manner similar to that described hereinbefore in Example 2, but using as the starting material the appropriate quantity of ethyl (E)-7-{1-(4-fluorophenyl)-3-isopropylpyrrolo[2,1-a]-phthalazin-2-yl}-3,5-dihydroxyhept-6-enoate (prepared as described in Example 3), there was prepared sodium (E)-7-{1-(4-fluorophenyl)-3-isopropylpyrrolo[2,1-a]-phthalazin-2-yl)-3,5-dihydroxyhept-6-enoate, in the form of a yellow solid, m.p. 226°–230° C. (with decomposition). [Elemental analysis: C, 61.2; H, 5.8; N, 5.2%; calculated: C, 61.2; H, 5.9; N, 5.3%; NMR (in a mixture of DMSO-d6 and $D_2O$): 1.1–1.32 (2 H, m), 1.47 (6 H, d, J=7 Hz), 1.8–2.16 (2 H, m), 3.56–3.86 (2 H, m), 4.04–4.20 (1 H, m), 5.28 and 5.37 (1 H, two dd, J=16 Hz, 6 Hz), 6.46 (1 H, dd, J=16 Hz, 1 Hz), 7.15–7.50 (7 H, m), 7.80–7.88 (1 H, m), 8.56 (1 H, s)].

The NMR spectrum indicated that the product was a 3:2 mixture of the erythro- and threo-diastereoisomers.

EXAMPLE 5

Compound E

A stirred solution of ethyl (E)-7-{1-(4-fluorophenyl)-3-isopropylpyrrolo[2,1-a]phthalazin-2-yl}-5- hydroxy-3-oxohept-6-enoate (3.98 g) in methanol (120 ml) under an argon atmosphere at 0°–5° C. was treated with sodium borohydride (243 mg). After 3 hours the solution was allowed to warm to room temperature, and was then evaporated to small volume (20 ml). The solution was treated with water (300 ml), and extracted with a mixture of diethyl ether and ethyl acetate (2×250 ml; 1:1 v/v). The combined extracts were dried over magnesium sulphate and evaporated, to give methyl (E)-7-{1-(4-fluorophenyl)-3-isopropylpyrrolo[2,1-a]-phthalazin-2-yl}-3,5-dihydroxyhept-6-enoate, in the form of an orange foam (3.16 g).

EXAMPLE 6

Compound F

A solution of methyl (E)-7-{1-(4-fluorophenyl)-3-isopropylpyrrolo[2,1-a]phthalazin-2-yl}-3,5-dihydroxyhept-6-enoate (3.16 g) in anhydrous diethyl ether (100 ml) was treated with activated manganese dioxide (12.61 g) and the mixture was stirred at room temperature under an argon atmosphere with the exclusion of light for 18 hours. The mixture was then filtered through diatomaceous earth. The filter pad was washed with diethyl ether (2×150 ml) and the combined filtrate and washings were concentrated to give an orange foam. This foam was subjected to flash chromatography on silica gel, using a mixture of diethyl ether and hexane (4:1 v/v) as eluant, to give methyl (E)-7-{1-(4-fluorophenyl)-3-isopropylpyrrolo[2,1-a]phthalazin-2-yl)-3-hydroxy-5-oxohept-6-enoate (1.61 g), in the form of an orange foam. [NMR (in $CDCl_3$): 1.59 (6H, d, J=8 Hz), 2.55 (4 H, m), 3.45–4.15 (5 H, m), 4.40 (1H, m), 5.82 (1H, d, J=16 Hz), 7.05–7.70 (8H, m), 7.85 (1H, d, J=16 Hz), 8.30 (1H, s)].

EXAMPLE 7

Compound G

By proceeding in a manner similar to that described hereinbefore in Example 2, but using as the starting material the appropriate quantity of methyl (E)-7-{1-(4-fluorophenyl)-3-isopropylpyrrolo[2,1-a]phthalazin-2-yl)-3-hydroxy-5-oxohept-6-enoate (prepared as described in Example 6), there was prepared sodium (E)-7-{1-(4-fluorophenyl)-3-isopropylpyrrolo[2,1-a]phthalazin-2-yl)-3-hydroxy-5-oxohept-6-enoate, thought to be in a hydrated form, m.p. 150°–157° C. (with decomposition).

EXAMPLE 8

Compounds CA and CB

Ethyl (E)-7-{1-(4-fluorophenyl)-3-isopropylpyrrolo[2,1-a]phthalazin-2-yl}-3,5-dihydroxyhept-6-enoate (1:1 g; prepared as described in Example 3) was subject to h.p.l.c. on a silica gel column using a mixture of hexane, chloroform and methanol (85:15:1 v/v) as eluant, to give ethyl erythro-(E)-7-{1-(4-fluorophenyl)-3-isopropylpyrrolo[2,1-a]phthalazin-2-yl}-3,5-dihydroxyhept-6-enoate (0.62 g) in the form of a yellow gum [NMR (in a mixture of CDCl$_3$ and D$_2$O): 1.28 (3H, t, J=7 Hz), 1.36–1.7 (8H, m), 2.43–2.49 (2H, m), 3.8 (1H, septet, J=7 Hz), 4.10–4.26 (3H, m), 4.3–4.45 (1H, m), 5.33 (1H, dd, J=16 Hz, 7 Hz), 6.64 (1H, dd, J=16 Hz, 1 Hz), 7.12–7.48 (7H, m), 7.57–7.65 (1H, m), 8.26 (1H, s)], and ethyl threo-(E)-7-{1-(4-fluorophenyl)-3-isopropylpyrrolo[2,1-a]phthalazin-2-yl}-3,5-dihydroxyhept-6-enoate (0.27 g) in the form of a yellow gum [NMR (in a mixture of CDCl$_3$ and D$_2$O): 1.28 (3H, t, J=7 Hz), 1.38–1.78 (8H, m), 2.41–2.48 (2H, m), 3.8 (1H, septet, J=7 Hz), 4.10–4.26 (3H, m), 4.34–4.48 (1H, m), 5.38 (1H, dd, J=16 Hz, 6 Hz), 6.67 (1H, dd, J=16 Hz, 1 Hz), 7.12–7.45 (7H, m), 7.58–7.66 (1H, m), 8.26 (1H, s)].

EXAMPLE 9

Compound DA

By proceeding in a manner similar to that described hereinbefore in Example 2, but using as the starting material the appropriate quantity of ethyl erythro-(E)-7-{1-(4-fluorophenyl)-3-isopropylpyrrolo[2,1-a]phthalazin-2-yl}-3,5-dihydroxyhept-6-enoate (prepared as described in Example 8), there was prepared sodium erythro-(E)-7-{1-(4-fluorophenyl)-3-isopropylpyrrolo[2,1-a]phthalazin-2-yl}-3,5-dihydroxyhept-6-enoate in the form of a yellow solid, m.p. 218°–222° C. (with decomposition) [NMR (in a mixture of DMSO-d$_6$ and D$_2$O): 1.1–1.56 (8H, m), 1.78–2.1 (2H, m), 3.54–3.85 (2H, m), 4.04–4.18 (1H, m), 5.31 (1H, dd, J=16 Hz, 6 Hz), 6.46 (1H, dd, J=16 Hz, 1 Hz), 7.09–7.50 (7H, m), 7.82–7.9 (1H, m), 8.58 (1H, s)].

EXAMPLE 10

Compound DB

By proceeding in a manner similar to that described hereinbefore in Example 2, but using as the starting material the appropriate quantity of ethyl threo-(E)-7-{1-(4-fluorophenyl)-3-isopropylpyrrolo[2,1-a]-phthalazin-2-yl}-3,5-dihydroxyhept-6-enoate (prepared as described in Example 8), there was prepared sodium threo-(E)-7-{1-(4-fluorophenyl)-3-isopropylpyrrolo[2,1-a]-phthalazin-2-yl}-3,5-dihydroxyhept-6-enoate in the form of a yellow solid, m.p. 218°–225° C. (with decomposition) [NMR (in a mixture of DMSO-d$_6$ and D$_2$O): 1.1–1.38 (2H, m), 1.48 (6H, d, J=7 Hz), 1.74–2.06 (2H, m), 3.66–3.85 (2H, m), 4.05–4.20 (1H, m), 5.35 (1H, dd, J=16 Hz, 6 Hz), 6.6 (1H, dd, J=16 Hz, 1 Hz), 7.15–7.50 (7H, m), 7.80–7.88 (1H, m), 8.58 (1H, s)].

REFERENCE EXAMPLE 1

(a) A stirred solution of phthalazine (3.25 g) and trimethylsilylcyanide (4.96 g) in dichloromethane (40 ml), containing a catalytic amount of anhydrous aluminium chloride (10 mg), was treated dropwise with isobutyryl chloride (5.3 g), keeping the temperature of the mixture below 32° C. The mixture was then stirred at the ambient temperature for 18 hours and then it was washed successively with water (50 ml), aqueous hydrochloric acid (1N; 2×30 ml), water (50 ml), aqueous sodium hydroxide solution (1N; 2×30 ml) and water (50 ml) and then it was dried over magnesium sulphate. The solution was evaporated and the resulting residue was triturated with a mixture of petroleum ether (b.p. 40°–60° C.) and diethyl ether (3:1 v/v; 30 ml). The solid which separated was collected and dried, to give 1-cyano-2-isobutyryl-1,2-dihydrophthalazine (5.56 g) in the form of a colourless solid, m.p. 144°–146° C. [Elemental analysis: C, 68.9; H, 5.61; N, 18.4%; calculated: C, 68.7; H, 5.77; N, 18.5%; NMR (in CDCl$_3$): 1.16 (3H, d, J=7 Hz), 1.27 (3H, d, J=7 Hz), 3.55 (1H, septet, J=7 Hz), 6.66 (1H, s), 7.36–7.44 (2H, m), 7.50–7.58 (2H, m), 7.73 (1H, s); Mass spectrum (electron impact) m/z=227].

(b) A stirred solution of 1-cyano-2-isobutyryl-1,2-dihydrophthalazine (12.6 g) in glacial acetic acid (50 ml) at 60° C. was treated with an aqueous solution of fluoroboric acid (48% w/v; 50 ml). After stirring for 15 minutes the mixture was chilled to 15° C. and stirring was continued for a further period of 1 hour. The solid which separated was collected, washed thoroughly with diethyl ether, and dried, to give 1-amino-3-isopropyloxazolo[4,3-a]phthalazinium tetrafluoroborate (15.58 g) in the form of a bright yellow solid, m.p. 180°–182° C. [NMR (in DMSO-d$_6$) : 1.42 (6H, d, J=7 Hz), 3.74 (1H, septet, J=7 Hz), 7.50–7.60 (1H, m), 7.85–8.05 (3H, m), 8.12 (2H, broad singlet), 8.99 (1H, s)].

(c) A mixture of 1-amino-3-isopropyloxazolo[4,3-a]phthalazinium tetrafluoroborate (1.58 g) and ethyl phenylpropiolate (1.74 g) in 1,3-dimethyl-imidazolin-2-one (30 ml) was maintained at 40° C. for 19 hours and then the resulting brown solution was poured into water (200 ml), and the mixture was extracted with a mixture of petroleum ether (b.p. 40°–60° C.) and diethyl ether (1:1 v/v; 3×200 ml). The extracts were combined, dried over magnesium sulphate, and evaporated, and the resulting residue was subjected to flash chromatography on silica gel, using as eluant a mixture of petroleum ether (b.p. 40°–60° C.) and diethyl ether (19:1 v/v), to give ethyl 3-isopropyl-1-phenylpyrrolo[2,1-a]phthalazine-2-carboxylate (0.72 g) in the form of a yellow solid, m.p. 141°–142° C. [Elemental analysis: C, 77.1; H, 6.24; N, 7.8%; calculated C, 77.1; H, 6.19; N, 7.8%; NMR (in CDCl$_3$) : 0.93 (3H, t, J=7 Hz), 1.57 (6H, d, J=7 Hz), 4.08 (2H, q, J=7 Hz), 4.35 (1H, septet, J=7 Hz), 7.23–7.50 (8H, m), 7.60–7.66 (1H, m), 8.35 (1H, s); Mass spectrum (electron impact) m/z=358].

(d) A stirred suspension of lithium aluminium hydride (1.0 g) in diethyl ether (40 ml) at 0° C. under an atmosphere of argon was treated with a solution of ethyl 3-isopropyl-1-phenylpyrrolo[2,1-a]phthalazine-2-carboxylate (2.35 g) in diethyl ether (60 ml). The reaction mixture was stirred at 0° C. for 2 hours and then it was quenched by dropwise treatment with ethyl acetate (50 ml). After stirring for a further period of 1 hour it was treated with saturated aqueous sodium sulphate solution (100 ml) and the resulting mixture was then extracted with ethyl acetate (3×100 ml). The combined extract was dried over magnesium sulphate and evaporated and the resulting residue was subjected to flash chromatography on silica gel, using as eluant a mixture of petroleum ether (b.p. 40°–60° C.) and diethyl ether (3:1 v/v), to give 2-hydroxymethyl-3-isopropyl-1-phenylpyrrolo[2,1-a]phthalazine (1.22 g) in the form of a yellow gummy solid. [NMR (in a mixture of CDCl$_3$ and D$_2$O): 1.57 (6H, d, J=7 Hz), 3.86 (1H, septet, J=7 Hz), 4.62 (2H, s), 7.25–7.53 (8H, m), 7.58–7.64 (1H, m), 8.3 (1H, s); Mass spectrum (electron impact) m/z=316].

(e) A mixture of 2-hydroxymethyl-3-isopropyl-1-phenylpyrrolo[2,1-a]phthalazine (1.22 g) and activated manganese dioxide (18 g) in diethyl ether (200 ml) was stirred at the ambient temperature under an atmosphere of argon for 24 hours. The suspension was then filtered and the solid was extracted with diethyl ether (3×50 ml). The extracts and filtrate were combined and evaporated, and the resulting residue was triturated with a mixture of petroleum ether (b.p. 40°–60° C.) and diethyl ether (8 ml; 3:1 v/v), to give 3-isopropyl-1-phenylpyrrolo[2,1-a]phthalazine-2carboxaldehyde (0.88 g) in the form of a yellow solid, m.p. 163°–164° C. [Elemental analysis: C, 80.4; H, 5.78; N, 8.8%; calculated: C, 80.2; H, 5.77; N, 8.9%; NMR (in CDCl$_3$): 1.52 (6H, d, J=7 Hz), 4.41 (1H, septet, J=7 Hz), 7.30–7.35 (3H, m), 7.42–7.50 (5H, m), 7.58–7.66 (1H, m), 8.34 (1H, s), 9.83 (1H, s); Mass spectrum (electron impact) m/z=314].

(f) A stirred suspension of sodium hydride (80% w/w dispersion in oil; 243 mg; 8.1 mmol) in dry tetrahydrofuran (20 ml) at −5° C. was treated dropwise with triethyl phosphonoacetate (1.82 g) under an atmosphere of argon, maintaining the temperature at −5° C. The resulting mixture was then stirred for 30 minutes and then it was treated with a solution of 3-isopropyl-1-phenylpyrrolo[2,1-a]]phthalazine-2-carboxaldehyde (0.85 g) in tetrahydrofuran (10 ml). The reaction mixture was stirred at 0° C. for 30 minutes and then at 60° C. for 2 hours and then it was quenched by treatment with saturated aqueous ammonium chloride solution (20 ml). The organic layer was separated and the aqueous phase was extracted with diethyl ether (2×20 ml). The combined organic layers were dried over magnesium sulphate and evaporated, and the residue was triturated with a mixture of petroleum ether (b.p. 40°–60° C.) and diethyl ether (10 ml; 3:1 v/v). The solid which separated was collected, to give ethyl (E)-3-(3-isopropyl-1-phenylpyrrolo[2,1-a]-phthalazin2-yl)propenoate (0.86 g) in the form of a yellow solid, m.p. 158°–159° C. [Elemental analysis: C, 77.7; H, 6.31; N, 7.2%; calculated: C, 78.1; H, 6.29; N, 7.3%; NMR (in CDCl$_3$): 1.24 (3H, t, J=7 Hz), 1.55 (6H, d, J=7 Hz), 3.88 (1H, septet, J=7 Hz), 4.14 (2H, q, J=7 Hz), 5.46 (1H, d, J=16 Hz), 7.14–7.33 (3H, m), 7.38–7.60 (6H, m), 7.86 (1H, d, J=16 Hz), 8.26 (1H, s); Mass spectrum (electron impact) m/z=384].

(g) A stirred solution of ethyl (E)-3-(3-isopropyl-1-phenylpyrrolo[2,1-a]phthalazin-2-yl)propenoate (0.86 g) in dry tetrahydrofuran (25 ml) at 0° C. under an atmosphere of argon was treated dropwise with a solution of diisobutyl aluminium hydride in tetrahydrofuran (1M; 6.7 ml). The reaction mixture was stirred at 0° C. for 1 hour and then it was quenched by dropwise treatment with saturated aqueous sodium sulphate solution (25 ml). The resulting mixture was partitioned between water (100 ml) and diethyl ether (100 ml), and the organic layer was separated. The aqueous layer was extracted with diethyl ether (2×100 ml) and the combined organic layers were dried over magnesium sulphate and evaporated, to give (E)-3-(3-isopropyl-1-phenylpyrrolo[2,1-a]phthalazin-2-yl)propen-1-ol (0.96 g), in the form of a yellow oil. [NMR (in a mixture of CDCl$_3$ and D$_2$O ): 1.54 (6H, d, J=7 Hz), 3.82 (1H, septet, J=7 Hz), 4.15 (2H, dd, J=7 Hz, 1 Hz), 5.55 (1H, dt, J=16 Hz, 7 Hz), 6.62 (1H, dt, J=16 Hz, 1 Hz), 7.21–7.32 (3H, m), 7.35–7.62 (6H, m), 8.23 (1H, s)].

(h) A mixture of activated manganese dioxide (2.18 g) and (E)-3-(3-isopropyl-1-phenylpyrrolo[2,1-a]-phthalazin-2-yl)propen-1-ol (0.77 g) in anhydrous diethyl ether (50 ml) was stirred at the ambient temperature under an atmosphere of argon for 2 hours. The suspension was then filtered and the solid was washed thoroughly with diethyl ether (4×25 ml). The filtrate was evaporated, to give a yellow oil, which was triturated with a mixture of petroleum ether (b.p. 40°–60° C.) and diethyl ether (5 ml; 3:1 v/v) and the solid which separated was collected, to give (E)-3-(3-isopropyl-1-phenylpyrrolo[2,1-a]phthalazin-2-yl)propenal (0.56 g) in the form of a yellow solid, m.p. 162°–164° C. [Elemental analysis: C., 81.5; H, 6.07; N, 8.2%; calculated: C, 81.1; H, 5.92; N, 8.2%; NMR (in CDCl$_3$): 1.6 (6H, d, J=7 Hz), 3.89 (1H, septet J=7 Hz), 5.83 (1H, dd, J=16 Hz, 8 Hz), 7.13–7.68 (10H, m), 8.29 (1H, s), 9.41 (1H, d, J=8 Hz); Mass spectrum (electron impact) m/z=340].

(i) A stirred suspension of sodium hydride (80% dispersion in oil, 112 mg; 3.7 mmol) in dry tetrahydrofuran (15 ml) was treated with ethyl acetoacetate (0.43 g) under an atmosphere of argon, maintaining the temperature at −10° C. The mixture was stirred for 30 minutes and then it was treated with a solution of butyl lithium in hexane (2.5M; 1.38 ml), still maintaining the temperature at −10° C. The mixture was stirred for a further period of 20 minutes and then it was treated dropwise with a solution of (E)-3-(3-isopropyl-1-phenylpyrrolo[2,1-a]phthalazin-2-yl)propenal (0.56 g) in tetrahydrofuran (5 ml) at −10° C., and the resulting mixture was stirred at −10° C. for 1 hour. The reaction mixture was then quenched at −10° C. by treatment with saturated aqueous ammonium chloride solution (15 ml). The mixture was allowed to warm to the ambient temperature and then it was partitioned between water (20 ml) and diethyl ether (50 ml). The organic layer was separated and the aqueous layer was extracted with diethyl ether (50 ml). The combined organic layers were dried over magnesium sulphate, evaporated and subjected to flash chromatography on silica gel, using as eluant a mixture of petroleum ether (b.p. 40°–60° C.) and diethyl ether (3:1 v/v), to give ethyl (E)-5-hydroxy-7-(3-isopropyl-1-phenylpyrrolo[2,1-a]phthalazin-2-yl)-3-oxohept-6-enoate (0.33 g) in the form of an orange oil. [NMR (in a mixture of CDCl$_3$ and D$_2$O): 1.27 (3H, t, J=7 Hz), 1.54 (6H, d, J=7 Hz), 2.52–2.62 (2H, m), 3.44 (2H, s), 3.78 (1H, septet, J=7 Hz), 4.21 (2H, q, J=7 Hz), 4.50–4.62 (1H, m), 5.3 (1H, dd, J=16 Hz, 7 Hz), 6.65 (1H, dd, J=16 Hz, 1 Hz), 7.22–7.62 (9H, m), 8.24 (1H, s)].

REFERENCE EXAMPLE 2

By proceeding in a manner similar to that described hereinbefore in Reference Example 1 sections (c) to (i), but replacing the ethyl phenylpropiolate, used as a starting material in section (c), by the appropriate quantity of methyl 4-fluorophenylpropiolate, there were prepared, respectively:

(a) methyl 1-(4-fluorophenyl)-3-isopropylpyrrolo[2,1-a]phthalazine-2-carboxylate in the form of a yellow solid, m.p. 148°–149° C. [Elemental analysis: C, 73.1; H, 5.3; N, 7.8%; calculated: C, 72.9; H, 5.29; N, 7.7%; NMR (in CDCl$_3$): 1.54 (6H, d, J=7 JHz), 3.62 (3H, s), 4.29 (1H, septet, J=7 Hz), 7.09–7.40 (7H, m), 7.56–7.65 (1H, m), 8.32 (1H, s)];

(b) 1-(4-fluorophenyl)-2-hydroxymethyl-3-isopropylpyrrolo[2,1-a]phthalazine in the form of a yellow gum. [NMR (in a mixture of CDCl$_3$ and D$_2$O): 1.55 (6H, d, J=7 Hz), 3.85 (1H, septet, J=7 Hz), 4.6 (3H, s), 7.13–7.50 (7H, m), 7.58–7.65 (1H, m), 8.29 (1H, s)];

(c) 1-(4-fluorophenyl)-3-isopropylpyrrolo[2,1-a]phthalazine-2-carboxaldehyde in the form of a yellow solid, m.p. 153°–155° C. [Elemental analysis: C, 76.0; H, 5.15; N, 8.2%; calculated: C, 75.9; H, 5.16; N, 8.4%;

NMR (in CDCl₃): 1.56 (6H, d, J=7 Hz), 4.38 (1H, septet, J=7 Hz); 7.13–7.47 (7H, m), 7.58–7.67 (1H, m), 8.34 (1H, s), 9.87 (1H, s); Mass spectrum (electron impact) m/z=332];

(d) ethyl (E)-3-{1-(4-fluorophenyl)-3-isopropylpyrrolo[2,1-a]phthalazin-2-yl}propenoate in the form of a yellow solid, m.p. 157°–158° C. [Elemental analysis: C, 74.5; H, 5.91; N, 6.7%; calculated: C, 74.6; H, 5.76; N, 7.0%; NMR (in CDCl₃): 1.26 (3H, t, J=7 Hz), 1.57 (6H, d, J=7 Hz), 3.88 (1H, septet, J=7 Hz), 4.17 (2H, q, J=7 Hz), 5.50 (1H, d, J=16 Hz), 7.14–7.44 (7H, m), 7.56–7.65 (1H, m), 7.87 (1H, d, J=16 Hz), 8.28 (1H, s); Mass spectrum (electron impact) m/z=402];

(e) (E)-3-{1-(4-fluorophenyl)-3-isopropylpyrrolo[2,1-a]phthalazin-2-yl}propen-1-ol in the form of an orange oil. [NMR (in a mixture of CDCl₃ and D₂O):- 1.57 (6H, d, J=7 Hz), 3.82 (1H, septet, J=7 Hz), 4.12 (2H, dd, J=6 Hz, 1 Hz), 5.54 (1H, dt, J=16 Hz, 6 Hz), 6.62 (1H, dt, J=16 Hz, 1 Hz), 7.10–7.44 (7H, m), 7.54–7.63 (1H, m), 8.24 (1H, s)];

(f) (E)-3-{1-(4-fluorophenyl)-3-isopropylpyrrolo[2,1-a]phthalazin-2-yl}propenal in the form of a yellow solid, m.p. 195°–197° C. [Elemental analysis: C, 77.0, H, 5.41; N, 7.6%; calculated: C, 77.1; H, 5.34; N, 7.82%; NMR (in CDCl₃): 1.59 (6H, d, J=7 Hz), 3.89 (1H, septet, J=7 Hz), 5.84 (1H, dd, J=16 Hz, 8 Hz), 7.12–7.43 (7H, m), 7.58–7.79 (2H, m), 8.31 (1H, s), 9.44 (1H, d, J=8 Hz); Mass spectrum (electron impact) m/z=358]; and (g) ethyl (E)-7-{1-(4-fluorophenyl)-3-isopropylpyrrolo[2,1-a]phthalazin-2-yl}-5-hydroxy-3-oxohept-6-enoate in the form of a yellow gum. [NMR (in a mixture of CDCl₃ and D₂O): 1.28 (3H, t, J=7 Hz), 1.53 (6H, d, J=7 Hz), 2.60–2.68 (2H, m), 3.45 (2H, s), 3.78 (1H, septet, J=7 Hz), 4.21 (2H, q, J=7 Hz), 4.50–4.64 (1H, m), 5.3 (1H, dd, J=16 Hz, 7 Hz), 6.67 (1H, dd, J=16 Hz, 1 Hz), 7.12–7.44 (7H, m), 7.54–7.63 (1H, m), 8.24 (1H, s)].

The present invention includes within its scope pharmaceutical compositions which comprise at least one of the compounds of formula I or a pharmaceutically acceptable salt thereof in association with a pharmaceutically acceptable carrier or coating. In clinical practice the compounds of the present invention may be administered parenterally, for example topically, especially when treating certain fungal infections, but are preferably administered rectally or, more preferably, orally.

Solid compositions for oral administration include compressed tablets, pills, powders and granules. In such solid compositions, one or more of the active compounds is, or are, admixed with at least one inert diluent such as starch, sucrose or lactose. The compositions may also comprise, as is normal practice, additional substances other than inert diluents, e.g. lubricating agents, such as magnesium stearate.

Liquid compositions for oral administration include pharmaceutically acceptable emulsions, solutions, suspensions, syrups and elixirs containing inert diluents commonly used in the art such as water and liquid paraffin. Besides inert diluents such compositions may comprise adjuvants, such as wetting and suspending agents, and sweetening, flavouring, perfuming and preserving agents. The compositions according to the invention for oral administration also include capsules of absorbable material such as gelatin, containing one or more of the active substances with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. The compositions may also contain adjuvants such as stabilising, preserving, wetting, emulsifying and dispersing agents. They may be sterilised, for example, by filtration through a bacteria-retaining filter, by incorporation in the compositions of sterilising agents, by irradiation or by heating. They may also be manufactured in the form of sterile solid compositions, which can be dissolved in sterile water or some other sterile injectable medium immediately before use.

Solid compositions for rectal administration include suppositories formulated in accordance with known methods and containing one or more of the compounds of formula I or a pharmaceutically acceptable salt thereof.

Compositions in the form of solutions or suspensions, if desired together with additives as described above, in vegetable or other greases, paraffin or other waxes or lacquers or creams, to be applied topically, are also included in the invention.

The percentage of active ingredient in the compositions of the invention may be varied, it being necessary that it should constitute a proportion such that a suitable dosage shall be obtained. Obviously, several unit dosage forms may be administered at about the same time. The dose, the route of administration and the duration of the treatment employed will be determined by the physician, and depend upon the desired therapeutic effect and the condition of the patient. In the adult, the doses are generally between 0.1 and 50, preferably between 0.2 and 8.5, mg/kg body weight per day by oral administration.

The following Examples illustrate pharmaceutical compositions according to the present invention.

COMPOSITION EXAMPLE 1

No. 2 size gelatin capsules each containing: 3:2 mixture of erythro- and threo-disastereoisomers of sodium (E)-7-(1-(4-fluorophenyl)-3-isopropylpyrrolo[2,1-a]phthalazin-2-yl)-3,5-dihydroxy

| hept-6-enoate | 20 mg |
| --- | --- |
| lactose | 100 mg |
| starch | 60 mg |
| dextrin | 40 mg |
| magnesium stearate | 1 mg | were prepared in accordance with the usual procedure.

COMPOSITION EXAMPLE 2

No. 2 size gelatin capsules each containing: sodium erythro-(E)-7-(1-{4-fluorophenyl)-3-isopropylpyrrolo[2,1-a]phthalazin-2-yl)-3,5-dihydroxy

| hept-6-enoate | 20 g |
| --- | --- |
| lactose | 100 mg |
| starch | 60 mg |
| dextrin | 40 mg |
| magnesium stearate | 1 mg | were prepared in accordance with the usual procedure.

The active ingredient may be replaced by the appropriate quantity of any other of the compounds of formula I.

We claim:

1. A pyrrolo[2,1-a]phthalazine of the formula:

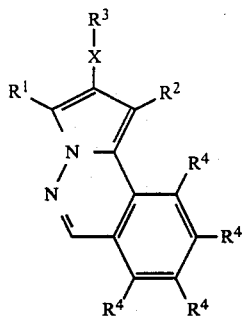

wherein $R^1$ and $R^2$, which may be the same or different, each represents a cycloalkyl group of 3 to 8 carbon atoms, or represents a straight- or branched-chain alkyl, alkenyl or alkynyl group of up to 6 carbon atoms which may be substituted by up to three halogen atoms or represents a phenyl group which is unsubstituted or substituted by one or more substituents selected from the group consisting of halogen atoms, cycloalkyl and cycloalkenyl groups each of 4 to 8 carbon atoms, and straight- or branched-chain alkyl, alkenyl or alkynyl groups each of up to 6 carbon atoms which are themselves unsubstituted or substituted by up to three substituents selected from the group consisting of halogen atoms and straight- or branched-chain alkoxy and alkylthio groups each of up to 6 carbon atoms, X represents an ethylene or vinylene group, $R^3$ represents a group of the formula:

$$-Y-CH_2-CH(OH)-CH_2-COOR^5 \qquad (II)$$

wherein Y represents a carbonyl or hydroxymethylene group and $R^5$ represents a hydrogen atom or an alkyl group of up to 6 carbon atoms which is unsubstituted or substituted by up to three substituents selected from the group consisting of halogen atoms and straight- or branched-chain alkoxy and alkylthio groups each of up to 6 carbon atoms, or $R^3$ represents a lactone ring of the formula:

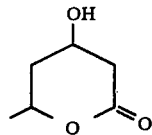

and the symbols $R^4$ may be the same or different and each represents a hydrogen or halogen atom or represents a straight- or branched-chain alkyl, alkanyl or alkynyl group of up to 6 carbon atoms which is unsubstituted or substituted by up to three substituents selected from the group consisting of halogen atoms and straight- or branched-chain alkoxy and alkylthio groups each of up to 6 carbon atoms, or a phenyl group which is unsubstituted or substituted by one or more substituents selected from the group consisting of halogen atoms, cycloalkyl and cycloalkenyl groups each of 4 to 8 carbon atoms, and straight- or branched-chain alkyl, alkenyl or alkynyl groups each of up to 6 carbon atoms which are themselves unsubstituted or substituted by up to three substituents selected from the group consisting of halogen atoms and straight- or branched-chain alkoxy and alkylthio groups each of up to 6 carbon atoms, or a group of the formula $R^6O-$ wherein $R^6$ represents a straight- or branched-chain alkyl group of up to 6 carbon atoms, a phenyl group or a phenylalkyl group of 1 or 2 carbon atoms in the alkyl moiety, or a pharmaceutically acceptable salt thereof when $R^5$ represents a hydrogen atom.

2. A compound according to claim 1 wherein $R^1$ and $R^2$ are different.

3. A compound according to claim 1 wherein X represents a vinylene group in the E configuration.

4. A compound according to claim 1 wherein halogen substituents on alkyl, alkenyl or alkynyl groups represented by $R^1$ or $R^2$ are chlorine or fluorine atoms.

5. A compound according to claim 1 wherein, when $R^3$ represents a group of formula (II) and Y represents a hydroxymethylene group, the compound is in the erythro-form.

6. A compound according to claim 1 wherein, when $R^3$ represents a group of formula (III) the hydroxy group attached to the lactone ring is in the trans-configuration with respect to the rest of the molecule.

7. A compound according to claim 1 wherein $R^3$ represents a group of the formula (III) which has the (4R,6S)-configuration when X represents vinylene and the (4R,6S)-configuration when X represents ethylene.

8. A compound according to claim 1 which exhibits one or more of the following features:
 (i) one of $R^1$ and $R^2$ represents an unsubstituted or substituted phenyl group and the other represents a cycloalkyl group of 3 to 8 carbon atoms, or a straight- or branched-chain alkyl, alkenyl or alkynyl group of up to 6 carbon atoms, which may be substituted by up to three halogen atoms;
 (ii) X represents a trans-vinylene group;
 (iii) $R^5$ represents a hydrogen atom or a methyl or ethyl group; and
 (iv) the symbols $R^4$ all represent hydrogen atoms.

9. A compound according to claim 1 which is a pharmaceutically acceptable salt of a pyrrolo[2,1-a]phthalazine derivative of formula (I) wherein $R^3$ represents a group of formula (II) in which Y is as defined in claim 1 and $R^5$ represents a hydrogen atom.

10. A compound according to claim 9 which is an alkali metal salt.

11. A compound according to claim 1 which is ethyl (E)-3,5-dihydroxy-7-(3-isopropyl-1-phenylpyrrolo[2,1-a]-phthalazin-2-yl)hept-6-enoate, ethyl (E)-7-{1-(4-fluorophenyl)-3-isopropylpyrrolo[2,1-a]phthalazin-2-yl}-3,5-dihydroxyhept-6-enoate, or methyl (E)-7-{1-(4-fluorophenyl)-3-isopropylpyrrolo[2,1-a]phthalazin-2-yl}-3,5-dihydroxyhept-6-enoate, or a threo or erythro diastereoisomer thereof; or methyl (E)-7-{1-(4-fluorophenyl)-3-isopropylpyrrolo[2,1-a]phthalazin-2-yl}-3-hydroxy- 5-oxohept-6-enoate or sodium (E)-7-{1-(4-fluorophenyl)-3-isopropylpyrrolo[2,1-a]phthalazin-2-yl}-3-hydroxy-5-oxohept-6-enoate.

12. A compound according to claim 1 which is sodium (E)-3,5-dihydroxy-7-(3-isopropyl-1-phenylpyrrolo[2,1-a]phthalazin-2-yl)hept-6-enoate or a threo or erythro diastereoisomer thereof.

13. A compound according to claim 1 which is sodium (E)-7-{1-(4-fluorophenyl)-3-isopropylpyrrolo[2,1-a]phthalazin-2-yl}-3,5-dihydroxyhept-6-enoate or a threo or erythro diastereoisomer thereof.

14. The erythro diastereoisomer according to claim 13.

15. A pharmaceutical composition useful in the treatment of hypercholesterolaemic and hyperlipoproteinaemic states and of atherosclerosis and associated conditions selected from the group consisting of angina, myocardial infarction, cerebral vascular occulsion, arterial aneurism, peripheral vascular disease, recurrent pancreatitis, xanthomas and fungal infections which comprises, as active ingredient, an effective amount of a pyrrolo[2,1-a]phthalazine of formula (I) as defined in claim 1, or a pharmaceutically acceptable salt thereof, in association with a pharmaceutically acceptable carrier or coating.

16. A method for the treatment of hypercholesterolaemic or hyperlipoproteinaemic states or of atherosclerosis or associated conditions selected from the group consisting of angina, myocardial infarction, cerebral vascular occulsion, arterial aneurism, peripheral vascular disease, recurrent pancreatitis, xanthomas and fungal infections in a patient which comprises administering to the patient an effective amount of a pyrrolo[2,1-a]phthalazine of formula (I) as defined in claim 1 or a pharmaceutically acceptable salt thereof.

* * * * *